US011052042B2

(12) United States Patent
Brueck-Scheffler

(10) Patent No.: US 11,052,042 B2
(45) Date of Patent: Jul. 6, 2021

(54) AQUEOUS SUSPENSIONS OF CICLESONIDE FOR NEBULISATION

(71) Applicant: Covis Pharma B.V., Baarn (NL)

(72) Inventor: Antje Brueck-Scheffler, Constance (DE)

(73) Assignee: Covis Pharma GMBH, Zug (CH)

(*) Notice: Subject to any disclaimer, the term of this patent is extended or adjusted under 35 U.S.C. 154(b) by 0 days.

(21) Appl. No.: 14/865,637

(22) Filed: Sep. 25, 2015

(65) Prior Publication Data

US 2016/0015634 A1 Jan. 21, 2016

Related U.S. Application Data

(62) Division of application No. 10/582,499, filed as application No. PCT/EP2004/053495 on Dec. 15, 2004, now abandoned.

(30) Foreign Application Priority Data

Dec. 16, 2003 (EP) .................................... 03028848

(51) Int. Cl.

| | |
|---|---|
| ***A61K 31/58*** | (2006.01) |
| ***A61K 9/50*** | (2006.01) |
| ***A61K 9/00*** | (2006.01) |
| ***C07J 71/00*** | (2006.01) |
| ***A61K 47/10*** | (2017.01) |
| ***A61K 47/26*** | (2006.01) |
| ***A61K 47/44*** | (2017.01) |
| ***A61K 47/12*** | (2006.01) |
| ***A61K 47/14*** | (2017.01) |

(52) U.S. Cl.

CPC ............ *A61K 9/0078* (2013.01); *A61K 31/58* (2013.01); *A61K 47/10* (2013.01); *A61K 47/12* (2013.01); *A61K 47/14* (2013.01); *A61K 47/26* (2013.01); *A61K 47/44* (2013.01); *C07J 71/00* (2013.01); *C07J 71/0005* (2013.01)

(58) Field of Classification Search

CPC .............................. A61K 9/0078; A61K 31/58
USPC ........................................... 514/174; 424/489
See application file for complete search history.

(56) References Cited

U.S. PATENT DOCUMENTS

| | | | |
|---|---|---|---|
| 4,787,536 | A | 11/1988 | Widerstrom |
| 5,346,702 | A | 9/1994 | Na et al. |
| 5,482,934 | A | 1/1996 | Calatayud et al. |
| 5,540,930 | A | 7/1996 | Guy et al. |
| 5,733,901 | A | 3/1998 | Gutterer |
| 5,747,061 | A | 5/1998 | Amselem et al. |
| 5,858,410 | A | 1/1999 | Muller et al. |
| 6,120,752 | A | 9/2000 | Oliver et al. |
| 6,241,969 | B1 | 6/2001 | Saidi et al. |
| 6,264,923 | B1 | 7/2001 | Oliver et al. |
| 6,392,036 | B1 | 5/2002 | Karlsson et al. |
| 6,464,958 | B1 | 10/2002 | Bernini et al. |
| 6,598,603 | B1 | 7/2003 | Andersson et al. |
| 6,667,344 | B2 | 12/2003 | Banerjee et al. |
| 6,939,559 | B1 | 9/2005 | Nishibe et al. |
| 6,967,017 | B1 | 11/2005 | Malvolti et al. |
| 2002/0183292 | A1 | 12/2002 | Pairet et al. |
| 2003/0103864 | A1 | 6/2003 | McAffer et al. |
| 2004/0023935 | A1 | 2/2004 | Banerjee et al. |
| 2004/0247628 | A1 | 12/2004 | Lintz et al. |
| 2005/0009923 | A1 | 1/2005 | Banerjee et al. |
| 2005/0115332 | A1 | 6/2005 | Ido et al. |
| 2005/0175546 | A1 | 8/2005 | Sambuco et al. |
| 2005/0244339 | A1 | 11/2005 | Jauernig et al. |
| 2005/0245493 | A1 | 11/2005 | Marx et al. |
| 2006/0166953 | A1 | 7/2006 | Nishibe et al. |
| 2007/0025923 | A1 | 2/2007 | Wurst et al. |

FOREIGN PATENT DOCUMENTS

| | | | |
|---|---|---|---|
| CA | 2 464 250 | A1 | 5/2003 |
| CA | 2 481 520 | A1 | 10/2003 |
| CN | 1379674 | A | 11/2002 |
| DE | 019541689 | A1 | 5/1996 |
| DE | 101 45 361 | A1 | 4/2003 |
| EP | 0233849 | B1 | 6/1991 |
| EP | 1 079 808 | B1 | 3/2001 |
| EP | 1 574 222 | A1 | 9/2005 |
| EP | 1 632 250 | A1 | 3/2006 |
| IL | 148691 | A | 12/2006 |
| IL | 148725 | A | 12/2006 |
| IL | 165666 | A | 4/2010 |
| JP | S62192322 | A | 8/1987 |
| JP | 2003512329 | A | 4/2003 |
| JP | 2003512330 | A | 4/2003 |
| JP | 2004/035441 | | 2/2004 |

(Continued)

OTHER PUBLICATIONS

Zhang et al. "Particle size and surfactant effects on chemical mechanical polishing of glass using silica-based slurry" Applied Optics, Oct. 2010, vol. 49, No. 28, pp. 5480-5485. (Year: 2010).*

Sis et al. "Effect of nonionic and ionic surfactants on zeta potential and dispersion properties of carbon black powders" Colloids and Surfaces A: Physiochem. Eng.Aspects, 2009, vol. 341, pp. 60-67. (Year: 2009).*

European Pharmacopoeia, vol. 5.0, Chapter 2.6.1. on "Sterility", p. 145-149, (2005).

(Continued)

*Primary Examiner* — Shengjun Wang

(74) *Attorney, Agent, or Firm* — Lowenstein Sandler LLP

(57) ABSTRACT

This invention relates to a method for the preparation of sterile aqueous suspensions of ciclesonide by sterilization with moist heat. The invention further relates to pharmaceutical compositions in particular to sterile aqueous suspensions of ciclesonide for administration by nebulization in the prophylaxis and/or treatment of respiratory diseases.

14 Claims, No Drawings

(56) References Cited

FOREIGN PATENT DOCUMENTS

| | | | |
|---|---|---|---|
| JP | 2005535565 | A | 11/2005 |
| WO | 94/22899 | A1 | 10/1994 |
| WO | 95/31964 | A1 | 11/1995 |
| WO | 98/09982 | A1 | 3/1998 |
| WO | 99/25359 | A1 | 5/1999 |
| WO | 99/53899 | A1 | 10/1999 |
| WO | 00/25746 | A2 | 5/2000 |
| WO | 01/28517 | A1 | 4/2001 |
| WO | 01/28562 | A1 | 4/2001 |
| WO | 01/28563 | A1 | 4/2001 |
| WO | 0247668 | A2 | 6/2002 |
| WO | 02/083113 | A2 | 10/2002 |
| WO | 03/035030 | A1 | 5/2003 |
| WO | 03/070285 | A1 | 8/2003 |
| WO | 03/086347 | A1 | 10/2003 |
| WO | 03/086437 | A1 | 10/2003 |
| WO | 2004/004739 | A1 | 1/2004 |
| WO | 2004/032980 | A1 | 4/2004 |
| WO | 2004/054545 | A1 | 7/2004 |
| WO | 2004/078102 | A2 | 9/2004 |
| WO | 2004/085460 | A1 | 10/2004 |
| WO | 2005/037246 | A2 | 4/2005 |
| WO | 2005/115332 | A2 | 12/2005 |
| WO | 2006/055632 | A2 | 5/2006 |

OTHER PUBLICATIONS

Dent, G., "Ciclesonide", Current Opinion Investig Drugs, vol. 3, No. 1, p. 78-83, (2002).
Illum, L., et al., "Surface area stability of micronized steroids sterilized by irradiation", Arch. Pharm. Chemi Sci. Ed., vol. 2, p. 167-174, (1974).
European Pharmacopoeia, vol. 5.0, Chapter 5.1.1. on "Methods of Preparation of Sterile Products", p. 445-447, (2005).
US Pharmacopoeia, vol. 26, Chapter 1211 on "Sterilization and Sterility Assurance of Compendial Articles", p. 2433-2439.
US Pharmacopoeia, vol. 26, Chapter 71 on "Sterility Tests", p. 2011-2016.
"Autoclave standard operating procedures", 2002, pp. 1-4. http://www.chembio.uoguelph.ca/sop/autoclave_use.htm Oct. 1, 2002.
Allen et al. "Inhaled corticosteroidss: past lessons and future issues", Supplement to The Journal of Allergy and Clinical Immunology, Sep. 2003, vol. 112, No. 3, pp. S1-S40.
ACS Registry, Feb. 1995, p. 1.

* cited by examiner

AQUEOUS SUSPENSIONS OF CICLESONIDE FOR NEBULISATION

This application was filed as a divisional of U.S. application Ser. No. 10/582,499, which was filed Jun. 9, 2006, under 35 U.S.C. 371 as a national stage of PCT/EP2004/053495, filed Dec. 15, 2004 and which claims priority to EP 03028848.4 filed Dec. 16, 2003, the entire contents of each of which are incorporated herein by reference in their entirety

FIELD OF THE INVENTION

This invention relates to a method for the preparation of sterile aqueous suspensions of ciclesonide by sterilization with moist heat. The invention further relates to pharmaceutical compositions in particular to aqueous suspensions of ciclesonide for administration by nebulization in the prophylaxis and/or treatment of respiratory diseases.

BACKGROUND

U.S. Pat. No. 5,482,934 discloses pregna-1,4-diene-3,20-dione-16-17-acetal-21 esters and their use in the treatment of inflammatory conditions. The compounds have the general structure:

Formula I

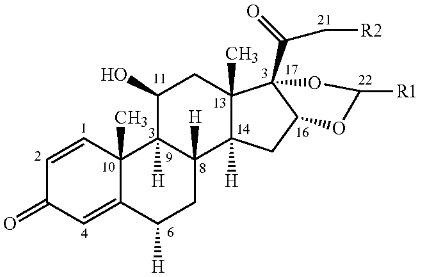

wherein R1 is 2-propyl, 1-butyl, 2-butyl, cyclohexyl or phenyl; and R2 is acetyl or isobutanoyl. Ciclesonide is the INN for a compound of formula I in which R1 is cyclohexyl and R2 is isobutanoyl with the chemical name [11β,16α(R)]-16,17-[(Cyclohexylmethylen)bis(oxy)]-11-hydroxy-21-(2-methyl-1-oxopropoxy)pregna-1,4-dien-3,20-dion.

This compound has undergone evaluation as an antiasthmatic and pharmacokinetic studies show that it will be useful in an inhaler formulation. Ciclesonide is only moderately absorbed after oral administration and has low systemic activity. Concentration of the drug in the lungs is high and metabolism by liver oxidases is very high, giving the drug a low plasma half-life. Systemic activity of ciclesonide is three times lower than that of budesonide, but anti-inflammatory activity is higher for the former.

Suitable formulations for pressurized metered dose inhalers (MDIs) for inhalation for ciclesonide are for example disclosed in U.S. Pat. Nos. 6,264,923 and 6,120,752.

Besides dry powder inhalers (DPIs) and pressurized metered dose inhalers (MDIs) nebulizers represent another class of devices allowing inhalative drug administration. Especially in case of children and elderly being not able to handle DPIs and MDIs correctly, nebulization is the preferred way of drug administration to the lungs. Thus it is desirable to provide ciclesonide in formulations suitable for administration by nebulization. Whereas in case of watersoluble drugs aqueous solutions are nebulized, this is not possible in case of water-insoluble drugs such as ciclesonide. Consequently these drug substances have to be applied in the form of suspensions. In order to allow deposition within the lungs the particle size of the aerosol droplets after nebulization needs to be in the range of approximately 1-7 μm. If suspensions will be administered, the particle size of the suspended drug particles is critical, since only particles being smaller than the aerosol droplets themselves are nebulized. For example micronized drug substance with a mean particle size of 2-6 μm is suitable for such suspensions.

Another requirement for suspension for nebulization is that these suspensions have to be isoosmotic in order to avoid irritation of the tissue coming into contact with the formulation.

In addition formulations for administration by nebulization have to be sterile. Whereas in case of solutions this can be achieved by sterilization of the final formulation by moist heat or by filtration through a bacteria retentive filter, achieving sterile suspensions with a defined particle size is more difficult. Sterilization by filtration is no option when micronized drug substance with a mean particle size of 2-6 μm is used, since the particles are not able to pass the filter.

Sterilization of the (powdered) drug substance by dry heat followed by preparation of the suspension under aseptic conditions represents another manufacturing method. This is only possible, if the drug substance is stable enough to withstand the high temperature during this sterilization process (according to European Pharmacopoeia 4.07, chapter 5.1.1. a temperature of 160° C. for at least 2 h is required). WO99/25359 describes a process for the sterilization of a powdered form of a glucocorticosteroid. WO99/25359 discloses that the sterilization process of glucocorticosteroids by dry heat can be carried out at a significantly lower temperature than that considered necessary for the heat sterilization of other substances. The drug substance is exposed to 110-120° C. for no longer than 10 h. WO99/25359 further discloses sterile pharmaceutical formulations comprising a glucocorticosteroid and one or more pharmaceutically acceptable additives, diluents or carriers. Examples of such additives include surfactants, pH regulating agents, chelating agents, agents rendering the suspension isoosmotic and thickening agents. These sterile formulations can be produced by mixing the sterilized glucocorticosteroid with any suitable additional ingredients, e.g. a surfactant, pH regulating or chelating agent, an agent rendering the suspension isoosmotic or a thickening agent. All components other than the glucocorticosteroid, can be produced by sterile filtration of their aqueous solutions. Examples 4 and 5 are related to sterile formulations comprising budesonide.

WO00/25746 discloses a process for preparing a sterile micronised glucocorticosteroid (beclomethasone dipropionate) by gamma-irradiation.

To provide the sterile aqueous suspension however it is needed that the suspension has to be prepared under aseptic condition throughout the manufacturing process with the sterilized ingredients including the steroid, indicating that a large and special manufacturing plant is necessary.

Another method for providing sterile aqueous pharmaceutical compositions is sterilization of the suspension by radiation. Ilium et al (Pharm. Chemi. Sci., Ed. 2, 1974, pp. 167-174) recommend a sterilization process for steroid-containing aqueous suspension by beta ray or gamma ray irradiation.

Another very common sterilization process for sterilizing of pharmaceutical compositions is autoclaving (sterilization by moist heat). Since the autoclaving is done by heating usually at 121° C., the method cannot be adopted for unstable drugs in the presence of water at such high temperature. In case of sterilization of the final suspension formulation by moist heat there is a considerable risk of an increase of the particle size during the sterilization process. Furthermore ciclesonide does not seem to be stable chemically at such high temperature, because ciclesonide has an acetal structure in its 16 and 17 positions.

WO 04/004739 is related to a ciclesonide-containing sterile aqueous suspension sterilized by autoclaving, wherein the concentration of ciclesonide after autoclaving is 95% or more comparing to that before autoclaving. It is further disclosed that it has been found that the uniformity of ciclesonide content can be maintained when hydroxypropylmethylcellulose is present in the suspension, even after sterilization by autoclaving.

Commercially available suspension formulations for glucocorticosteroids for nebulization are e.g. available under the tradenames Pulmicort™ and Flixotide™. Pulmicort™ nebules contain budesonide as drug substance. Besides the drug substance the suspension is composed of sodium chloride (agent to adjust osmolality) polysorbate 80 (suspending agent), sodium EDTA (chelating agent) citric acid/sodium citrate (buffering agent) and water. Flixotide™ nebules contain fluticasone propionate. Besides the drug substance the suspension is composed of sodium chloride (agent to adjust osmolality), polysorbate 20 and sorbitan monolaurate (suspending agents), monosodium phosphate dihydrate and dibasic sodium phosphate anhydrous (buffering agent) and water. This formulation and its preparation are also disclosed in WO95/31964. On page 4 it is stated that bulk suspensions are sterilized by means of thermal sterilisation using steam.

It is an object of the present invention to provide an aqueous suspension containing ciclesonide, in particular a sterile aqueous suspension, which is suitable for inhalative administration.

When autoclaving aqueous suspensions of ciclesonide for nebulization containing excipients usually present in formulations for nebulisation (such as sodium chloride as agent to adjust osmolality), clogging of ciclesonide particles is observed during sterilization process, making the suspension no longer suitable for inhalative application.

DESCRIPTION OF THE INVENTION

Surprisingly it has been found now that sterile aqueous suspensions of ciclesonide comprising agents for adjusting osmolality can be prepared by autoclaving aqueous suspension of ciclesonide when using nonionic agents for adjusting the osmolality as excipients in the suspension. No clogging of ciclesonide particles and no significant increase of the particle size of ciclesonide during the sterilization process is observed.

Subject of the present invention is therefore a method for preparing a sterile aqueous suspension of ciclesonide suitable for nebulization comprising the steps of:

(a) providing an aqueous suspension of ciclesonide, containing at least one non-ionic agent for adjusting the osmolality and optionally further pharmaceutically acceptable excipients and (b) autoclaving the aqueous suspension provided in (a).

Ciclesonide is the INN for an active compound having the chemical name [11α,16α-(R)]-16,17-[(cyclohexylmethylene)bis(oxy)]-11-hydroxy-21-(2-methyl-1-oxopropoxy) pregna-1,4-diene-3,20-dione. Ciclesonide and its preparation are described in U.S. Pat. No. 5,482,934. According to the invention, the name ciclesonide also includes solvates of ciclesonide, physiologically functional derivatives of ciclesonide or solvates thereof. Physiologically functional derivatives of ciclesonide, which can be mentioned in connection with the present invention, are preferably chemical derivatives of ciclesonide, which have a similar physiological function as ciclesonide or an active metabolite of ciclesonide, for example the 21-hydroxy derivative of ciclesonide (hereinafter also referred to as desisobutyryl-ciclesonide=des-CIC). The 21-hydroxy compound has the chemical name 16α,17-(22R,S)-cyclohexylmethylenedioxy-11β,21-dihydroxypregna-1,4-diene-3,20-dione. This compound and its preparation are disclosed in WO 94/22899. According to the invention, the name "ciclesonide" is understood as meaning not only the pure R epimer of the compound [11β,16α]16,17-[(cyclohexylmethylene)bis(oxy)]-11-hydroxy-21-(2-methyl-1-oxopropoxy) pregna-1,4-diene-3,20-dione but also R/S epimer mixtures in any desired mixing ratio (that is the compounds [11β,16α(R)]-16,17-[(cyclohexylmethylene)bis(oxy)]-11-hydroxy-21-(2-methyl-1-oxopropoxy)pregna-1,4diene3,20-dione and [11β,16α(S)]-16,17-[(cyclohexylmethylene)bis(oxy)]-11-hydroxy-21-(2-methyl1-oxopropoxy)pregna-1,4-diene-3,20-dione), those being preferred which essentially consist of R epimers. According to the invention, essentially consisting of R epimers means that the proportion of S epimers in the mixture is less than or equal to 5%, preferably less than or equal to 1%.

The mean particle size of ciclesonide present in the aqueous suspension is preferably within a range, which allows effective administration of ciclesonide by nebulisation. Preferably the mean particle size of ciclesonide (as determined by laser diffraction) is less than 12 μm, preferably from 0.1 to 8 μm, preferably 1 to 6 μm, particularly preferably 2 to 4 μm Ciclesonide with such particle size can be obtained by micronization of ciclesonide particles with greater particle size obtained in the manufacturing process of ciclesonide (e.g. as described in WO98/009982) or directly by crystallization processes leading to the desired mean particle size.

The amount of ciclesonide, or a pharmaceutical acceptable salt, solvate or physiologically functional derivative thereof which is required to achieve a therapeutic effect will, of course, vary with the subject under treatment, and the particular disorder or disease being treated. It will further depend on the efficiency of the nebulizer used and the deposition of the aerosol droplets in the lung. Suitable concentrations of ciclesonide within the suspension for nebulization can be in the range of 0.005% to 0.5% (w/v) (i.e. 0.05 mg/ml to 5 mg/ml).

Non-ionic agent for adjusting the osmolality in connection with the invention refers to pharmaceutically acceptable agent, which is of non-ionic nature and which is customarily used to render the Pharmaceutical solutions and/or suspensions isoosmotic with body fluids. Examples for non-ionic agents for adjusting the osmolality, which can be used in connection with the present invention, are selected from the group of mannitol, glycerol, glucose, lactose, trehalose, sucrose, propylene glycol, sorbitol, xylitol, polyethylene glycol, ethanol, isopropanol, cyclodextrins, derivatives of cyclodextrines and mixtures thereof. Preferred examples are mannitol, glycerol, glucose or mixtures thereof. The aim of adding an agent for adjusting the osmolatity is to provide a suspension according to the invention, which is isoosmotic or close to isoosmotic with body fluids, namely 290 mosmol/kg. In a preferred embodiment of the invention the non-ionic agent for adjusting osmolality is present in such an amount in the suspension according to the invention to provide an osmolality of the suspension in the range of 225-430 mosmol/kg, preferably in the range of 250 to 350 mosmol/kg, particularly preferably in the range of 280 to 300 mosmol/kg. As the person skilled in the art will appreciate the amount of agents needed to adjust the osmolality will depend on the presence of other excipients within the formulation contributing to the overall osmolality of the formulation.

Besides ciclesonide and the non-ionic agent to adjust the osmolality the suspension used in the process according to the invention may contain one ore more additional suitable excipients.

Suitable excipients, which can be mentioned include suspending agents, agents for modifying the pH of the suspension, chelating agents and optionally preservatives. In this connection it has been found that ionic excipients, (e.g. ionic buffer systems), should be avoided in the process according to the invention as these can lead to increase of particle size and clogging of ciclesonide in the suspension during autoclaving process. In a preferred embodiment according to the invention suitable excipients are selected from the group of non-ionic excipients.

In another embodiment the present invention therefore relates to a method for preparing a sterile aqueous suspension of ciclesonide suitable for nebulization comprising the steps of:

a. providing an aqueous suspension of ciclesonide, containing one or more pharmaceutically acceptable excipients, which one or more excipients are all non-ionic excipients; and
b. autoclaving the aqueous suspension provided in (a).

Suspending agents are used to obtain a uniform distribution of single particles of ciclesonide within the formulation resulting in a homogenous suspension. Examples for suspending agents, which can be mentioned in connection with the invention include polyoxyethylene sorbitan fatty acid esters (polysorbates), alkyl aryl polyether alcohols such as tyloxapol, poloxamers, poloxamines, polyoxyethylene castor oil derivatives, phospholipids, hydroxypropylmethylcellulose, hydroxypropylcellulose, hydroxyethylcellulose, methylcellulose, polyvinylpyrrolidone, polyvinylalcohol and mixtures thereof. Preferred suspending agents are polyoxyethylene castor oil derivatives, poloxamers, polysorbates, tyloxapol and mixtures thereof. Particularly preferred suspending agents are polysorbates, e.g. polysorbate 20 (=polyoxyethylene 20 sorbitan monolaurate), polysorbate 80 (=polyoxyethylene 20 sorbitan monooleate).

The concentrations of the suspending agents used within the formulation are largely depended on the concentration of the suspended drug substance. The suspending agent is added in an amount to achieve effective suspension of ciclesonide to provide a homogeneous suspension. The ratio between drug substance and suspending agent can usually vary from 0.05 to 50.

If necessary, agents for modifying the pH of the suspension can be added. Suitable examples, which may be mentioned are for example inorganic and organic acids selected from the group of hydrochloric acid, phosphoric acid, sulphuric acid, citric acid, tartaric acid, lactic acid and mixtures thereof. Preferably organic acids are present. As ciclesonide is known to be unstable under alkaline conditions the pH-value of the suspension should preferably be adjusted to yield neutral or slightly acidic conditions.

Chelating agents such as editic acid or edetate salts can be added in suitable concentrations (e.g. 0.01-0.1%). They can serve as antioxidant synergists by sequestering the traces of heavy metals thereby improving the chemical stability of the drug substance or of the excipients. In addition, they have some antimicrobial activity.

Optionally the formulation according to the invention might contain one or more preservatives although made sterile by the process according to the present invention. It is preferred to have a preservative present in the formulations according to the invention in order to preserve the microbiological quality during use. This is especially important in case of multiple dose vials. Suitable preservatives for example are benzoic acid, sorbic acids and its salts, propionic acid and its salts, phenol and derivatives such as cresol and chlorocresol, chlorobutanol, benzyl alcohol, phenyl ethyl alcohol, butyl paraben and propyl paraben.

Preferred formulations according to the invention contain the following components suspended/dissolved in water for injections:

| | | |
|---|---|---|
| Ciclesonide micronized | 0.025-0.1% | (w/v) |
| Glycerol | 2.5% | (w/v) |
| Polysorbate 20 | 0.0125-0.05% | (w/v) |
| Ciclesonide micronized | 0.025-0.1% | (w/v) |
| Glycerol | 2.5% | (w/v) |
| Polysorbate 80 | 0.0125-0.05% | (w/v) |
| Ciclesonide micronized | 0.025-0.1% | (w/v) |
| Mannitol | 5.0% | (w/v) |
| Polysorbate 20 | 0.0125-0.05% | (w/v) |
| Ciclesonide micronized | 0.025-0.1% | (w/v) |
| Mannitol | 5.0% | (w/v) |
| Polysorbate 80 | 0.0125-0.05% | (w/v) |

In another aspect the present invention relates to a sterile aqueous suspension of ciclesonide suitable for nebulization containing one or more pharmaceutically acceptable excipients, which one or more excipients are all non-ionic excipients.

In a further aspect the invention also relates to a sterile aqueous suspension of ciclesonide, containing at least one non-ionic agent to adjust the osmolality and optionally further pharmaceutically acceptable excipients. Preferably the sterile aqueous suspension is obtainable by a method of preparation according to the present invention. In one embodiment according to the invention the sterile aqueous suspension does not contain a preservative.

In another aspect the invention relates to an aqueous suspension of ciclesonide for administration by nebulization, wherein the concentration of ciclesonide within the suspension for nebulization is in the range of 0.005% to 0.5% (w/v) (i.e. 0.05 mg/ml to 5 mg/ml). In a preferred embodiment the suspension is a sterile suspension.

Suspensions used in the process according to the invention can be prepared by conventional methods for the preparation of suspension formulations. In a preferred embodiment of the invention the suspensions used in the process according to the invention can be prepared by dissolving the non-ionic agent for adjusting the osmolality and optionally other excipients (e.g. suspension agent) in purified water or water for injections. If desired, this solution of excipients can be filtered (sterile filtration). Ciclesonide with a suitable particle size is homogenously suspended within the solution (e.g. by stirring or by employing a turboemulsifier, eg Ultraturrax). The final formulation is filled into suitable containers (e.g. vials), sealed and sterilized by moist heat. Alternatively the formulation can be sterilized by moist heat as bulk and afterwards filled into sterile vials under aseptic conditions and sealed. Instead of glass vials containers prepared by a form-fill-seal process are also suitable. In this case the formulation can be sterilized by moist heat as bulk and filled under aseptic conditions afterwards. Filling into form-fill-seal containers and terminal sterilization by moist heat is also possible.

Sterilization by moist heat or autoclaving in connection with the present invention refers to a method of sterilizing in a suitable autoclaving equipment by steam with high pressure and temperature which meets the criteria according to US Pharmacopoeia 26, chapter 1211 "Sterilization and sterility assurance of compendial articles", European Pharmacopeia (Ph. Eur. 4.07, chapter 5.1.1. "Methods of preparation of sterile products"), or other Pharmacopoeias. Sterile aqueous suspension in this context refers to an aqueous suspension which meets the criteria according to US Pharmacopoeia 26 chapter 71 "Sterility tests", European Pharmacopeia (Ph. Eur. 4.07 chapter 2.6.1. <<Sterility" . . . ), or other Pharmacopoeias.

In connection with the process according to the invention it is preferred to expose the formulation to a temperature above 90° C., preferably 120° C., particularly preferably of at least 121° C. In a still preferred embodiment the formulation according to the invention is exposed to a temperature of at least 121° C. for at least 15 min in the presence of saturated steam under pressure. Other suitable combinations of temperatures (e.g. temperatures below 90° C.) and time may be used as well as long as they lead to a sterile formulation as required by the standards set in the various pharmacopoeias.

Further subject of the invention is a process comprising the steps of (a) dissolving the non-ionic agent for adjusting the osmolality and optionally other excipients in water;
(b) optionally filtering the solution;
(c) homogeneously suspending ciclesonide within the solution and
(d) autoclaving the aqueous suspension provided in (c).

[Amounts Expressed in Percent (%) Refer to Percent of Weight, Based on the Total Weight of the Formulation (w/v) Unless Stated Differently].

The invention will now be illustrated by the following examples without restricting it.

EXAMPLES

Example 1

2.5 kg of glycerol and 12.5 g of Polysorbate 80 are dissolved in 100 liters of water for injections. The solution is filtered through a filter with a pore size of 0.2 μm. 25 g of micronized ciclesonide is added and the suspension is stirred for at least 1 hour in order to yield a homogenous suspension. The suspension is filled into glass vials. Each vial contains 2 ml of the suspension. The vials are sterilized within an autoclave at a temperature of 121° C. for 15 min in the presence of saturated steam.

Example 2

5 kg of mannitol and 25 g of Polysorbate 20 are dissolved in 100 liters of water for injections. The solution is filtered through a filter with a pore size of 0.2 μm. 50 g of micronized ciclesonide is added and the suspension is stirred for at least 1 hour in order to yield a homogenous suspension. The suspension is filled into glass vials. Each vial contains 2 ml of the suspension. The vials is sterilized within an autoclave at a temperature of 121° C. for 15 min in the presence of saturated steam.

Example 3

5.5 kg of glucose and 12.5 g of Tyloxapol are dissolved in 100 liters of water for injections. The solution has been filtered through a filter with a pore size of 0.2 μm. 25 g of micronized ciclesonide is added and the suspension is stirred for at least 1 hour in order to yield a homogenous suspension. The suspension is filled into glass bottles containing each about 1 liter. The bottles are sterilized within an autoclave at a temperature of 121° C. for 20 min in the presence of saturated steam. After the sterilization process the sterile suspension is filled in a form-fill-seal process under aseptic conditions. The final product is composed of 2 ml of the suspension in a form-fill-seal container made from polyethylene or polypropylene.

Example 4

5 kg of mannitol and 25 g of Polysorbate 20 are dissolved in 100 liters of water for injections. The pH of the solution is adjusted to pH 6 by addition of citric acid. The solution is filtered through a filter with a pore size of 0.2 μm. 50 g of micronized ciclesonide is added and the suspension is stirred for at least 1 hour in order to yield a homogenous suspension. The suspension is filled into glass vials. Each vial contains 2 ml of the suspension. The vials are sterilized within an autoclave at a temperature of 115° C. for 40 min in the presence of saturated steam.

Comparative Examples

Example 5

Suspensions containing 0.05% of micronized ciclesonide, 0.025% of Polysorbate 20 (Formulation I), Polysorbate 80 (Formulation II) or Cremophor RH40 (Formulation III) as suspending agents and 0.9% of sodium chloride as agent for adjusting the osmolality in water for injections have been prepared. The suspensions have been filled into glass vials and have been sterilized by moist heat (121° C., 20 min). Prior to the sterilization and afterwards the size of the suspended particles has been measured by laser diffraction (Particle sizer series 2600, Malvern, suspension diluted with Polysorbate 80 solution 0.1% in water, calculation according to Fraunhofer, ultrasound applied if necessary). d10, d50 and d90 values are presented in the table below. d10, d50 and d90 values in connection with this invention mean, that for 10, 50 or 90% of the total volume of particles the size is lower. Prior to the measurements the samples were shaken in order to resuspend sedimented particles.

| | Prior to sterilization | | | After sterilization | | |
|---|---|---|---|---|---|---|
| Formulation | d10 [μm] | d50 [μm] | d90 [μm] | d10 [μm] | d50 [μm] | d90 [μm] |
| I | 1.98 | 4.15 | 8.83 | 13.53 | 80.06 | 110.12 |
| II | 2.27 | 4.74 | 9.32 | 11.39 | 79.01 | 109.92 |
| III | 2.05 | 4.29 | 8.81 | 10.37 | 74.05 | 108.88 |

As indicated in the table for all suspensions an increase of particles was detected after the sterilization. Large, clogged agglomerates of particles have been visible.

Example 6

Suspensions containing 0.05% of micronized ciclesonide, 0.025% of Polysorbate 20 as suspending agent and 2.5% of glycerol (Formulation IV), 5% of mannitol (Formulation V) or 5% of glucose (Formulation VI) as agent for adjusting the osmolality in water for injections have been prepared. The suspensions have been filled into glass vials and have been sterilized by moist heat (121° C., 20 min). Prior to the sterilization and afterwards the size of the suspended particles has been measured by laser diffraction (Mastersizer 2000, Malvern, suspension diluted with water, calculation according to Mie, assumed refractive index of suspended particles 1.52). Prior to the measurements the samples were shaken in order to resuspend sedimented particles. d10, d50 and d90 values are presented in the table below.

| | Prior to sterilization | | | After sterilization | | |
|---|---|---|---|---|---|---|
| Formulation | d10 [μm] | d50 [μm] | d90 [μm] | d10 [μm] | d50 [μm] | d90 [μm] |
| IV | 0.432 | 2.357 | 4.854 | 1.260 | 2.317 | 3.980 |
| V | 0.447 | 2.260 | 4.638 | 1.248 | 2.281 | 3.871 |
| VI | 0.461 | 2.424 | 4.943 | 1.268 | 2.713 | 6.036 |

As shown in the table there is no significant increase of the particle size when non-ionic agents for adjusting the osmolality are employed. The purity of ciclesonide in all formulations after the sterilization analysed by HPLC was higher than 99.5% indicating that the drug substance is stable.

Example 7

Suspensions containing 0.05% of micronized ciclesonide, 0.025% of Polysorbate 20 as suspending agent and 0.9% of sodium chloride (Formulation I) as ionic agent for adjusting the osmolality or no ionic agent at all (Formulation VII) have been prepared. The suspensions have been filled into glass vials and have been sterilized by moist heat (121° C., 20 min). Prior to the sterilization and afterwards the size of the suspended particles has been measured by laser diffraction (Mastersizer 2000, Malvern, suspension diluted with water, calculation according to Mie, assumed refractive index of suspended particles 1.52). Before the measurements the samples were shaken in order to resuspend sedimented particles. d10, d50 and d90 values are presented in the table below.

| | Prior to sterilization | | | After sterilization | | |
|---|---|---|---|---|---|---|
| Formulation | d10 [μm] | d50 [μm] | d90 [μm] | d10 [μm] | d50 [μm] | d90 [μm] |
| I | 0.382 | 2.581 | 5.623 | Large white agglomerates | | |
| VII | 0.393 | 2.508 | 5.483 | 1.259 | 2.268 | 3.887 |

As shown in the table the suspension containing no ionic agent for adjusting the osmolality did not show any significant increase of the particle size after the sterilization process.

Example 8

In order to evaluate if the sterilized suspensions with non-ionic agents for adjusting the osmolality are stable with regard to the particle size during storage, the particle size of the suspensions has been measured after 4 weeks storage at room temperature. Before the measurements the samples were shaken in order to resuspend sedimented particles.

| | Initial | | | After 4 weeks storage | | |
|---|---|---|---|---|---|---|
| Formulation | d10 [μm] | d50 [μm] | d90 [μm] | d10 [μm] | d50 [μm] | d90 [μm] |
| IV | 1.260 | 2.317 | 3.980 | 1.349 | 2.430 | 4.087 |
| V | 1.248 | 2.281 | 3.871 | 1.320 | 2.374 | 3.991 |
| VI | 1.268 | 2.713 | 6.036 | 1.223 | 2.727 | 6.236 |

No significant change of the particle size has been observed during the storage indicative for the good stability of the suspension formulations.

Example 9

Ciclesonide suspensions containing 0.05% of micronized ciclesonide have been prepared by the method described in example 1 and 2. In addition, citric acid has been added to adjust be pH of the suspension. Prior to and after sterilization the particle size of the samples has been measured by the method described in example 6.

| | Prior to sterilization | | | After sterilization | | |
|---|---|---|---|---|---|---|
| | d10 [μm] | d50 [μm] | d90 [μm] | d10 [μm] | d50 [μm] | d90 [μm] |
| Polysorbate 20 0.025%<br>Mannitol 5%<br>Citric acid to pH 4 | 0.455 | 2.355 | 4.894 | 1.302 | 2.806 | 6.573 |
| Polysorbate 20 0.025%<br>Mannitol 5%<br>Citric acid to pH 5 | 0440 | 2.351 | 4.810 | 1.299 | 2.636 | 5.002 |
| Polysorbate 20 0.025%<br>Mannitol 5%<br>Citric acid to pH 6 | 0.468 | 2.471 | 5.137 | 1.266 | 2.765 | 6.785 |
| Polysorbate 20 0.025%<br>Mannitol 5%<br>pH 7, no citric acid | 0.475 | 2.428 | 5.033 | 1.325 | 2.529 | 4.379 |

As a result no significant change of the particle size after the sterilization process has been observed.

Example 10

Ciclesonide suspensions containing 0.05% of micronized ciclesonide have been prepared by the method described in example 5 and 6. In addition, citric acid buffers pH5 (citric acid/sodium citrate) at various concentrations have been added to the suspensions. Prior to and after sterilization the particle size of the samples has been measured by the method described in example 6.

| | Prior to sterilization | | | After sterilization | | |
|---|---|---|---|---|---|---|
| | d10 [μm] | d50 [μm] | d90 [μm] | d10 [μm] | d50 [μm] | d90 [μm] |
| Polysorbate 20 0.025%<br>Mannitol 5%<br>Citric acid buffer 0.0001 mol/l | 0.468 | 2.445 | 5.041 | 1.250 | 2.886 | 9.170 |
| Polysorbate 20 0.025%<br>Mannitol 5%<br>Citric acid buffer 0.001 mol/l | 0.484 | 2.545 | 5.241 | 1.270 | 4.479 | 21.788 |
| Polysorbate 20 0.025%<br>Mannitol 5%<br>Citric acid buffer 0.01 mol/l | 0.468 | 2.445 | 5.041 | 1.527 | 6.798 | 47.779 |

The measured particle sizes prior and after sterilization indicate that with increasing buffer concentration the particle size after sterilization increases. This shows that the suspensions containing ionic buffering agents are susceptible to particle growth during the sterilization process.

Example 11

Suspensions containing 0.05% of micronized ciclesonide, 0.025% of Polysorbate 20 as suspending agent and 2.5% of glycerol (Formulation IV) or 5% of mannitol (Formulation V) as agent for adjusting the osmolality in water for injections have been prepared. The suspensions have been filled into glass vials and have been sterilized by moist heat at 110° C. for 120 min. Prior to and after sterilization the particle size of the samples has been measured by the method described in example 6.

|  | Prior to sterilization | | | After sterilization at 110° C., 120 min | | | After approx. 5 months storage at room temperature | | |
| --- | --- | --- | --- | --- | --- | --- | --- | --- | --- |
|  | d10 [µm] | d50 [µm] | d90 [µm] | d10 [µm] | d50 [µm] | d90 [µm] | d10 [µm] | d50 [µm] | d90 [µm] |
| Tween 20 0.025% Glycerol 2.5% | 0.932 | 2.093 | 4.138 | 1.388 | 2.500 | 4.204 | 1.314 | 2.505 | 4.483 |
| Tween 20 0.025% Mannitol 5% | 0.785 | 1.825 | 4.133 | 1.269 | 2.415 | 4.255 | 1.255 | 2.388 | 4.352 |

As a result no significant change of the particle size after the sterilization process and after approx. 5 months storage of the sterile formulations at room temperature has been observed.

Commercial Utility

The aqueous suspension of ciclesonide according to the invention can be used for the prophylaxis or treatment of a clinical condition in a mammal, such as a human (also referred to as patient), for which a glucocorticosteroid is indicated. Accordingly, the present invention provides a method for the prophylaxis or treatment of a clinical condition in a mammal, such as a human, for which a glucocorticosteroid is indicated, which comprises administration of a therapeutically effective amount of an aqueous suspension of ciclesonide, in particular a sterile aqueous suspension of ciclesonide according to the invention.

The aqueous suspension of ciclesonide according to the invention is particularly suitable in the prophylaxis and/or treatment of respiratory diseases. Respiratory disease according to the invention includes in particular diseases associated with inflammatory airway diseases and/or reversible airways obstruction such as asthma, nocturnal asthma, exercise-induced asthma, chronic obstructive pulmonary diseases (COPD) (e. g. chronic and wheezy bronchitis, emphysema), croup, respiratory tract infection and upper respiratory tract disease (e. g. rhinitis, such as allergic and seasonal rhinitis).

The aqueous suspensions according to the invention are particularly suitable for intrapulmonal administration in particular through administration by nebulization. The suspension may also be administered by any other suitable route. For administration by nebulization the suspension according to the invention can be nebulized by means of suitable nebulizer, for example a nebulizer connected to a compressor, (=jet nebulizer) (e.g. nebulizers: Pari LC Star™, Pari LC Plus™, Omron VC™, Sidestream MS 2400 and 2200™, Halolite™, Circulaire™ and compressors: eg Pari Proneb™ Ultra, DeVilbriss Pulmo Aide™, Medic Aid Portaneb™ Invacare Envoy™, MPV Truma MicroDrop™) and new generation nebulizers with different operation principles (e.g. Eflow™ by PARI, Omron U22 and Microair™ by Omron, AeroNeb™ by Aerogen, Touchspray™ by Odem, Microhaler™ by Pfeiffer).

Administration by nebulization is particularly suitable for the treatment of patients suffering from a respiratory disease and having difficulties to correctly use other devices for inhalation such as infants and young children or elderly being not able to handle DPIs and MDIs correctly. Preferably the patient in connection with the invention is a child. Child in connection with the invention refers to a human below eighteen years (e.g. seventeen years, fifteen years, ten years, nine years, five years, two years, 6 months etc.). Preferably child refers to a pre-pubertal human, and in particular to a human from 6 months to 10 years of age, in particular 12 months to 8 years of age.

The amount of ciclesonide, or a pharmaceutical acceptable salt, solvate or physiologically functional derivative thereof which is required to achieve a therapeutic effect will, of course, vary with the patient under treatment, and the particular disorder or disease being treated. As a monotherapy, ciclesonide is generally administered to patients by inhalation at a daily dose of from 0.05 mg to 2 mg, preferably 0.1 to 1 mg, which can be administered in one or several doses. The dose is preferably a daily dose and administered once or twice daily, preferably once daily. A once daily dose may be administered any time of the day, e.g. in the morning or preferably in the evening. The administration of a daily dose of ciclesonide is preferably part of a continuous treatment regimen, preferably a treatment period of more than one day, particularly preferably more than one week, e.g. a two week treatment period, a one month treatment period, a one year treatment period or a life long treatment period. The dosage of each administration can be the same or varied throughout the continuous treatment regimen.

Further subject of the invention is a drug product comprising a sealed container containing an aqueous suspension according to the invention and a label indicating administration by nebulization in a continuous treatment regimen. The container can be of any suitable kind, e.g. a form-fill-seal container made from polyethylene or polypropylene.

What is claimed is:

1. A sterile aqueous suspension of ciclesonide suitable for nebulization comprising
   ciclesonide having a mean particle size of about 0.1 to 8 µm,
   water,
   an effective amount of at least one non-ionic isotonization agent for adjusting the osmolality of the suspension to about 225-430 mosmol/kg, wherein the non-ionic isotonizing agent is selected from the group consisting of mannitol, glycerol, glucose, and mixtures thereof, an effective amount of suspending agent for homogenously suspending the ciclesonide in the sterile aqueous suspension, wherein the suspending agent comprises polysorbate, and at least one non-ionic pharmaceutically acceptable excipient, wherein the at least one non-ionic pharmaceutically acceptable excipient comprises citric acid in an amount to adjust the pH-value of the sterile aqueous suspension to pH of 4 to 7, wherein the sterile aqueous suspension does not comprise sodium chloride and hydroxypropylmethylcellulose, and wherein the aqueous suspension is sterilized using moist heat.

2. The sterile aqueous suspension according to claim 1, wherein the ciclesonide has a mean particle size of about 1 to 6 μm.

3. The sterile aqueous suspension according to claim 1, wherein the ciclesonide has a mean particle size of about 2 to 4 μm.

4. The sterile aqueous suspension according to claim 1, wherein the at least one non-ionic pharmaceutical excipient is selected from the group consisting of agents for modifying pH, chelating agents, preservatives, and mixtures thereof.

5. The sterile aqueous suspension according to claim 4, wherein the suspension also includes an agent for modifying pH that is an organic acid selected from the group consisting of tartaric acid, lactic acid, and mixtures thereof.

6. The sterile aqueous suspension according to claim 5, wherein the suspending agent further comprises tyloxapol, poloxamers, polyoxyethylene castor oil derivatives, or mixtures thereof.

7. The sterile aqueous suspension according to claim 1, wherein the ciclesonide concentration is about 0.005% to 0.5% w/v.

8. The sterile aqueous suspension according to claim 6, wherein the ciclesonide concentration is about 0.005% to 0.5% w/v.

9. The sterile aqueous suspension according to claim 1, wherein the d90 mean particle size of the ciclesonide in the sterile aqueous suspension remains less than 12 μm after 4 weeks of storage at room temperature.

10. The sterile aqueous suspension according to claim 1, wherein the citric acid is present in the sterile aqueous suspension in an amount to adjust the pH-value of the sterile aqueous suspension to pH of 5.

11. The sterile aqueous suspension according to claim 1, wherein the ratio between ciclesonide to suspending agent ranges from 0.05 to 50.

12. The sterile aqueous suspension according to claim 1, wherein the citric acid is present in an amount of up to about 0.001 mol/l in the sterile aqueous suspension.

13. The sterile aqueous suspension according to claim 1, wherein the osmolality of the suspension ranges from 250 mosmol/kg to 350 mosmol/kg.

14. The sterile aqueous suspension according to claim 1, wherein the aqueous suspension is sterilized using moist heat at 110° C. for 120 min.

* * * * *